United States Patent
Fiechter et al.

(10) Patent No.: US 11,229,458 B2
(45) Date of Patent: Jan. 25, 2022

(54) DEVICE FOR RECONSTRUCTING A SPINOUS PROCESS AND SPINAL FIXING EQUIPMENT COMPRISING SAID DEVICE

(71) Applicant: MEDACTA INTERNATIONAL S.A., Castel San Pietro (CH)

(72) Inventors: Meinrad Fiechter, Lugano (CH); Michele Incandela, Como (IT); Massimiliano Martis, Cassina Rizzardi (IT); Francesco Siccardi, Castel San Pietro (CH)

(73) Assignee: MEDACTA INTERNATIONAL S.A., Castel San Pietro (CH)

( * ) Notice: Subject to any disclaimer, the term of this patent is extended or adjusted under 35 U.S.C. 154(b) by 458 days.

(21) Appl. No.: 15/781,125

(22) PCT Filed: Nov. 29, 2016

(86) PCT No.: PCT/IB2016/057175
§ 371 (c)(1),
(2) Date: Jun. 2, 2018

(87) PCT Pub. No.: WO2017/093886
PCT Pub. Date: Jun. 8, 2017

(65) Prior Publication Data
US 2018/0344360 A1    Dec. 6, 2018

(30) Foreign Application Priority Data
Dec. 3, 2015    (IT) .................. 102015000079759

(51) Int. Cl.
*A61B 17/70* (2006.01)
*A61F 2/44* (2006.01)

(52) U.S. Cl.
CPC ...... *A61B 17/7049* (2013.01); *A61B 17/7032* (2013.01); *A61B 17/7062* (2013.01); *A61F 2/44* (2013.01); *A61B 17/7034* (2013.01)

(58) Field of Classification Search
CPC ............. A61B 17/7049; A61B 17/705; A61B 17/7055; A61B 17/7032; A61B 17/7034; A61B 17/7062
(Continued)

(56) References Cited

U.S. PATENT DOCUMENTS

| 6,419,703 B1 | 7/2002 | Fallin et al. |
| 2005/0177240 A1 | 8/2005 | Blain |

(Continued)

FOREIGN PATENT DOCUMENTS

| FR | 2743290 A1 | 7/1997 |
| JP | 2011500292 A | 1/2011 |

OTHER PUBLICATIONS

International Search Report for PCT/IB2016/057175, dated Feb. 20, 2017, 2 pages.
(Continued)

*Primary Examiner* — Eduardo C Robert
*Assistant Examiner* — Christina Negrellirodriguez
(74) *Attorney, Agent, or Firm* — Meunier Carlin & Curfman LLC

(57) ABSTRACT

A device for reconstructing a spinous process, the device comprising a main portion having at least a first engaging hole; one fixing bar transversely insertable into the engaging hole; and said main portion having at least one through-seat for inserting ligaments to be reconstructed. Other aspects are disclosed and claimed.

16 Claims, 6 Drawing Sheets

(58) Field of Classification Search
USPC .......................................................... 606/250
See application file for complete search history.

(56) References Cited

U.S. PATENT DOCUMENTS

| | | | |
|---|---|---|---|
| 2008/0086124 A1* | 4/2008 | Forton | A61B 17/7055 606/60 |
| 2008/0177326 A1 | 7/2008 | Thompson | |
| 2008/0281360 A1 | 11/2008 | Vittur et al. | |
| 2012/0109202 A1* | 5/2012 | Kretzer | A61B 17/7049 606/248 |
| 2015/0032161 A1* | 1/2015 | Purcell | A61B 17/7055 606/265 |

OTHER PUBLICATIONS

English Translation of Notice of Reasons of Refusal issued in JP 2018-528756, dated Mar. 6, 2020.
Japanese Office Action for Application No. 2018-528756, dated Sep. 13, 2019, 6 pages.
English Translation of Notice of Reasons of Refusal issued in JP 2018-528756, dated Jul. 20, 2020.
English Translation of Decision of Dismissal of Amendment issued in JP 2018-528756, dated Jul. 20, 2020.

* cited by examiner

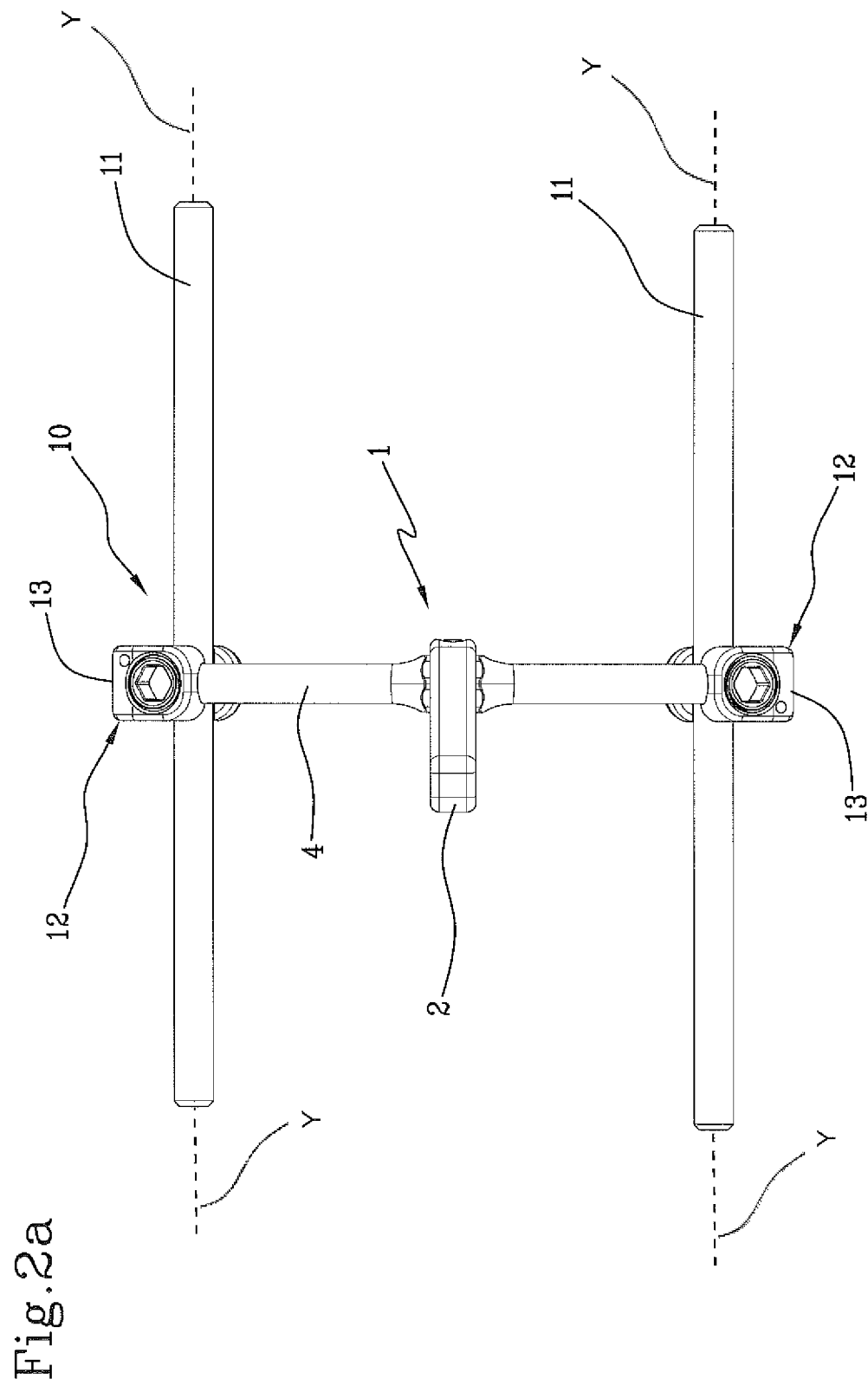

DEVICE FOR RECONSTRUCTING A SPINOUS PROCESS AND SPINAL FIXING EQUIPMENT COMPRISING SAID DEVICE

The present application is a National Phase Entry of PCT International Application No. PCT/IB2016/057175, which was filed on Nov. 29, 2016, and which claims priority to Application No. 102015000079759 filed in Italy on Dec. 3, 2015, the contents of which are hereby incorporated by reference.

The present invention relates to a device for reconstructing a spinous process and a spinal fixing equipment comprising said device. Therefore, the present invention finds particular application in the biomedical field and, especially, in the manufacturing of fastening and reconstruction systems for spinal surgery.

As known, the fastening devices are used in orthopaedic surgery to stabilize bones such as those of the spine, providing support in the event of damage to the spine itself.

In case of fractures or bone resections, it may be necessary to restore the correct bone anatomy not only for aesthetic reasons but mainly to restore the correct functioning of essential elements, such as ligaments.

In the specific case of bone resection, reduction or repositioning of the spinous process, it may be necessary to replace the bone and the ligament attachment points. By reconstructing the spinous process, the natural bone appearance is restored, as well as the correct behaviour of the ligaments.

Currently, in case of fractures of the spinous process, the same is reconstructed through fusion devices of the spinous process which distract and/or immobilize the spinous processes of adjacent vertebrae, as described in patent US2015164656.

In this way, the spine is excessively immobilized, fusing together parts that may instead be left more movable.

The Applicant has found that the known devices present drawbacks related to excessive limitation of mobility of the vertebrae, even of those not directly involved.

Therefore, the Applicant has assessed that it would be much more beneficial to be able to reconstruct the spinous process without tightening two adjacent vertebrae together, in order to reduce patient discomfort.

Therefore, the object of the present invention is to provide a device for reconstructing a spinous process, capable of overcoming the above mentioned drawbacks of the prior art.

More precisely, the object of the present invention is to provide a device for reconstructing a spinous process of simple positioning and effective use.

In addition, it is an object of the present invention to make available a reconstruction device of a spinous process which allows to restore both the appearance and, above all, the functionality of the spinous process, especially referring to the correct functionality of the ligaments.

Lastly, it is an object of the present invention to provide a reconstruction device of a spinous process that is minimally invasive and which does not produce undue discomfort to the patient.

These and other objects are substantially achieved by a device for reconstructing a spinous process as described in one or more of the appended claims. The dependent claims correspond to some possible embodiments of the invention.

In any case, these and further features, as well as their technical advantages, will become more apparent from the following exemplifying, and not limiting, description of a preferred, and therefore not exclusive, embodiment of a device for reconstructing a spinous process.

This description is provided with reference to the accompanying figures, provided only as an example and not as a limitation, in which:

FIGS. 2 and 2a are respectively a perspective view and a top view of a spinal fastening equipment comprising the device shown in FIG. 1;

Figure 1:
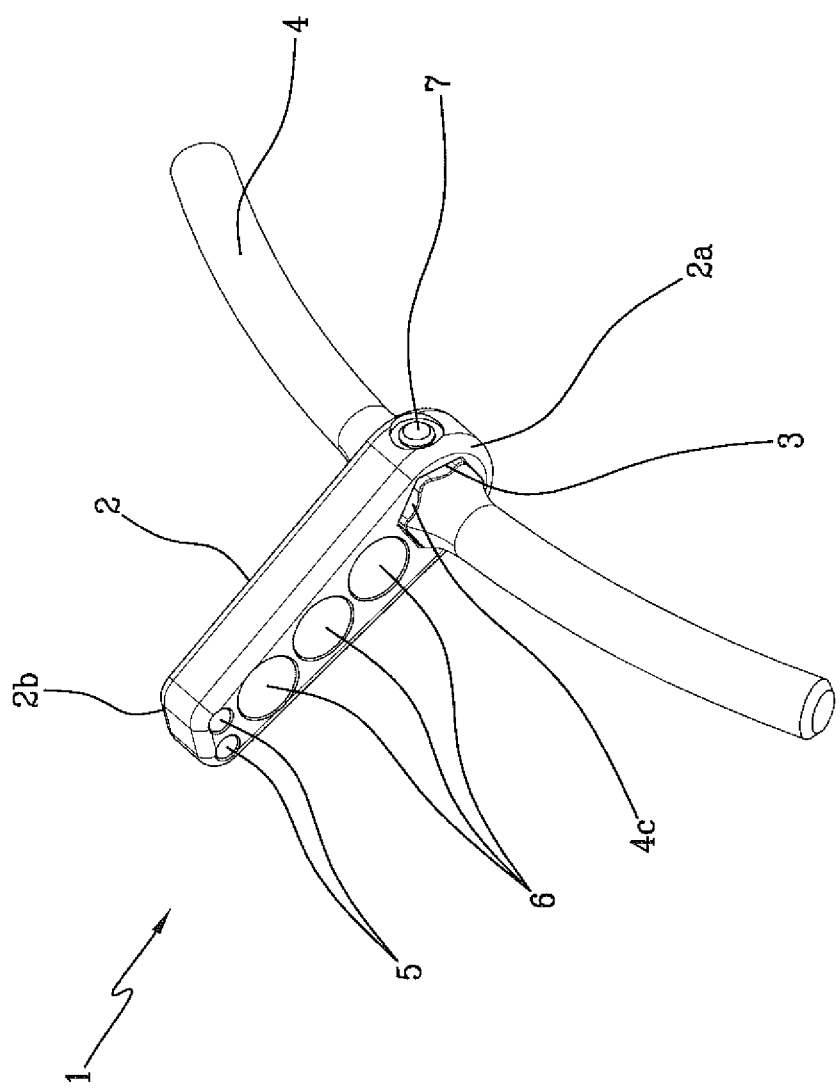
FIG. 1 is a prospective view of a device for reconstructing a spinous process according to the present invention.
Figure 1A:
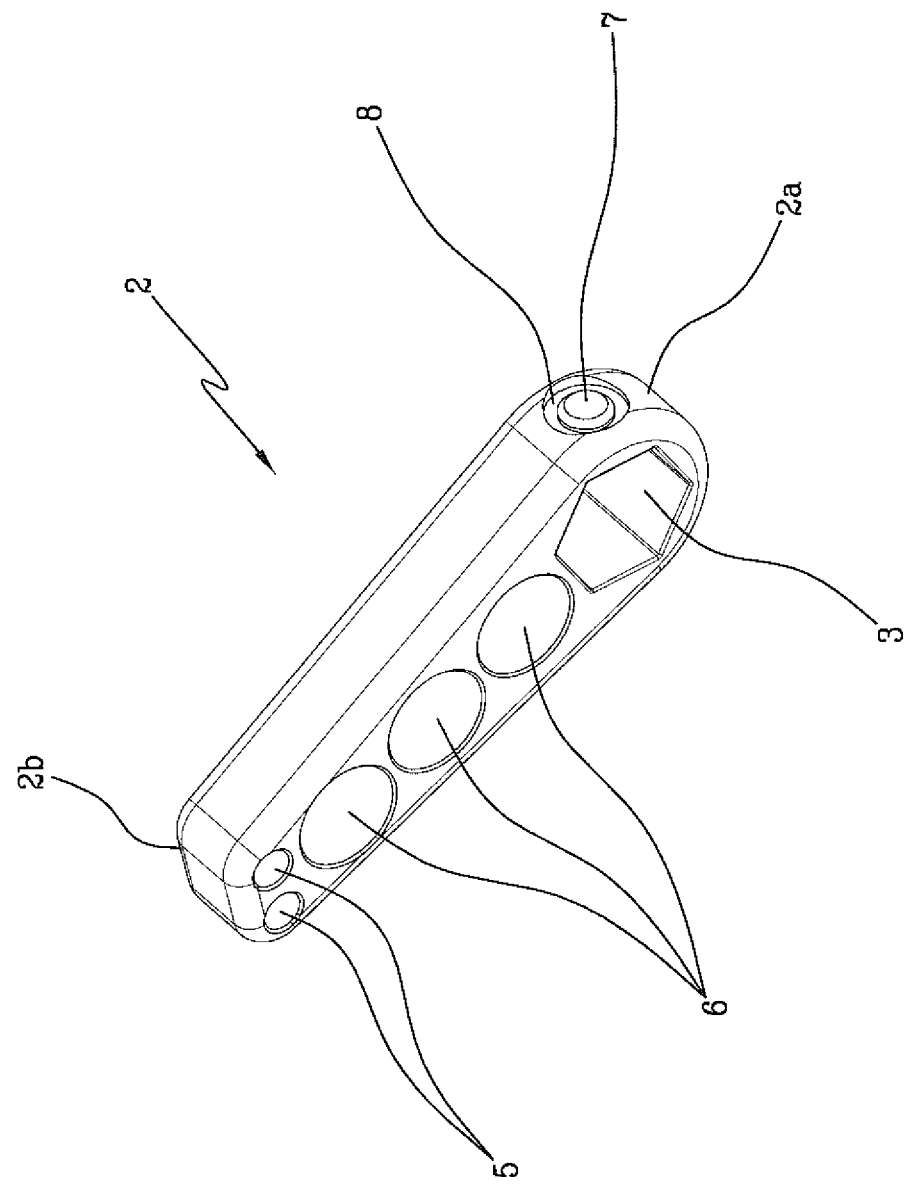
FIG. 1a is a detail of the device illustrated in FIG. 1.
Figure 2:
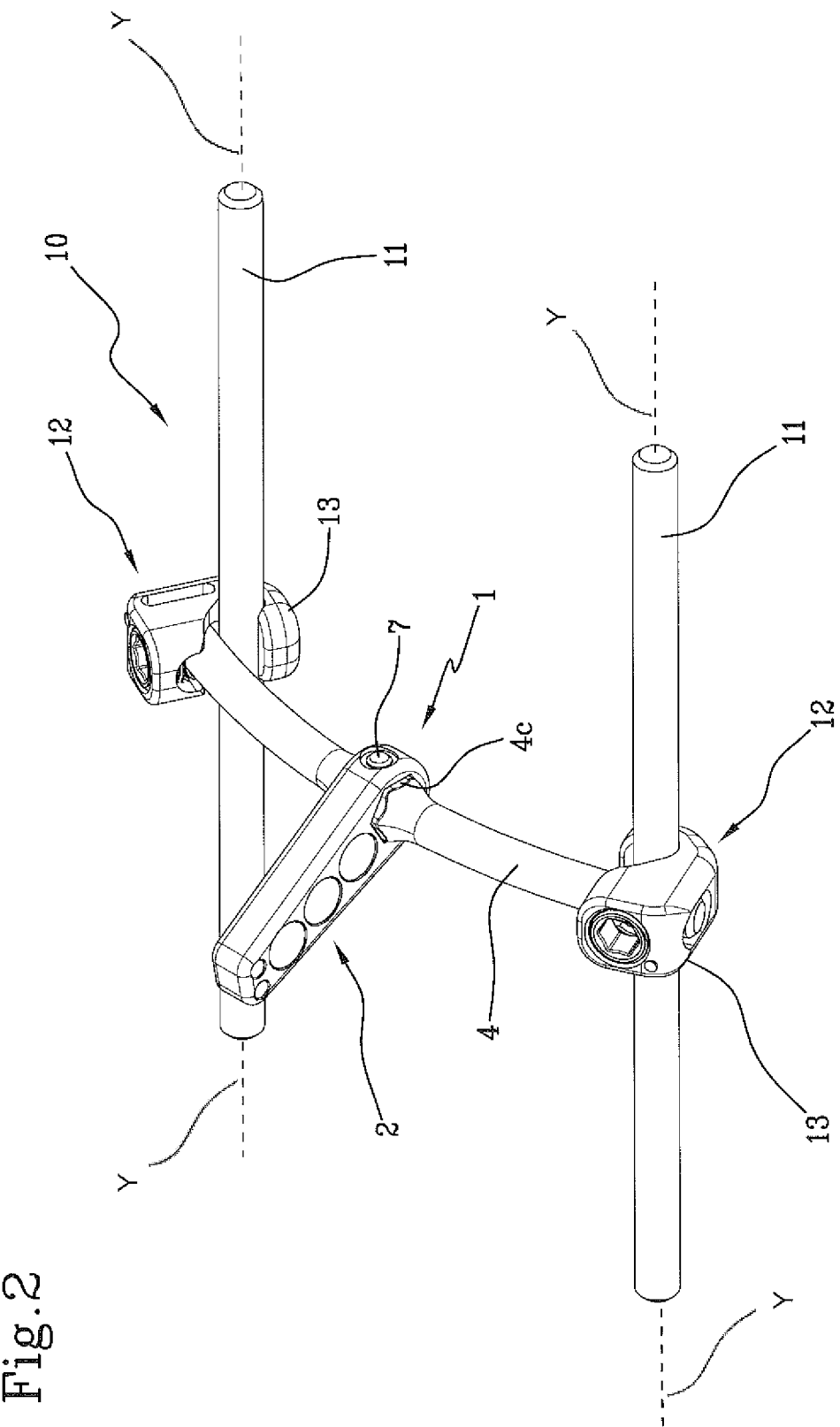
Figure 3:
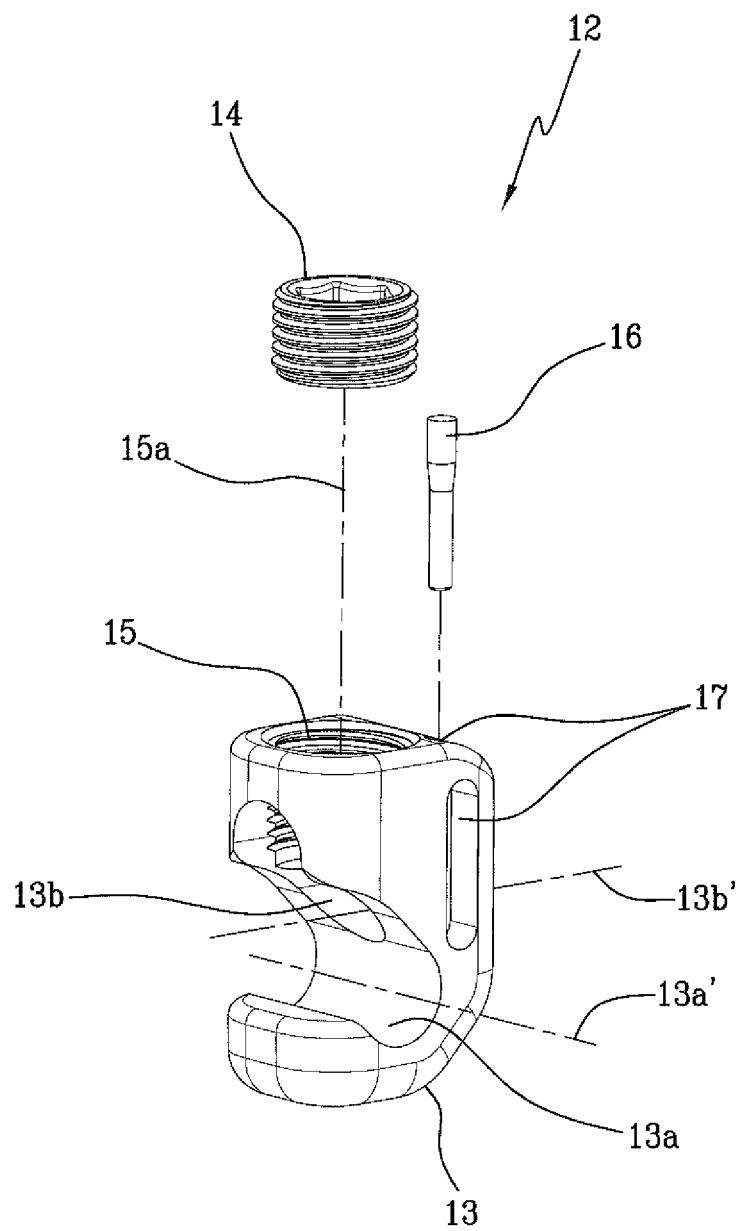
FIGS. 3 and 4 are perspective views of a detail of the spinal fastening equipment illustrated in FIGS. 1a and 2.
Figure 4:
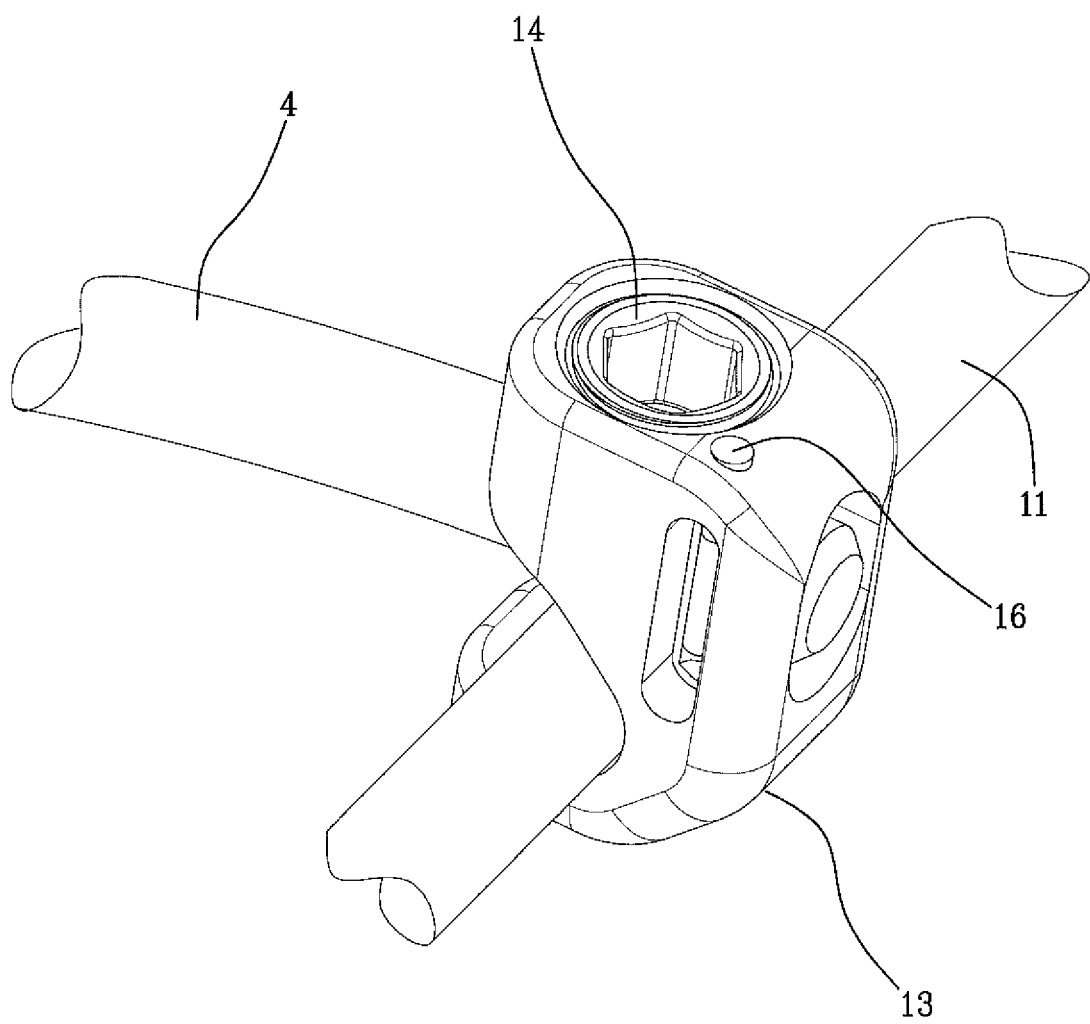

With reference to the attached figures, number 1 generally identifies a device for reconstructing a spinous process.

The device 1 for reconstructing a spinous process comprises a main portion 2 having an enlarged area 2a and a narrow area 2b. Preferably, the enlarged area 2a degrades continuously in the narrow area 2b conferring to the main portion 2 a substantially tapered shape.

At least one first coupling hole 3, for the insertion of a fixing bar 4, and at least one through-seat 5, for the insertion of ligaments to be reconstructed, are provided in the main portion 2. The fixing bar 4 is an integral part of the reconstruction device 1 and preferably presents a slightly curved configuration, specifically bow-shaped.

The fixing bar 4 is insertable transversely inside said engaging hole 3 of the main portion 2.

The engaging hole 3 is advantageously obtained in the enlarged area 2a of the main portion 2 and preferably presents a polygonal geometry which is compatible and which is matchable with a coupling portion 4c of the mentioned fixing bar 4. The coupling portion 4c preferably presents a polygonal geometry complementarily shaped to the engaging hole 3. The polygonal, preferably hexagonal, geometry prevents the relative rotation between the main portion 2 and the fixing bar 4.

Advantageously, the coupling portion 4c is arranged centrally with respect to the longitudinal extension of the fixing bar 4, in such a way that the main portion 2 is centred along the fixing bar 4.

A fastening pin 7, inserted in a respective seat 8 formed in the main portion, in correspondence of the enlarged area 2a, blocks the main portion 2 in a defined position along the axis of the transverse fixing bar 4 to prevent medio-lateral movements.

Ligaments are linked to the distal part of the main portion 2, in correspondence of the through-seat 5, preferably placed at the ends of the narrow area 2b. Advantageously, there are two or more through-seats 5 for the attachment of ligaments.

The shape of the main portion 2 artificially defines the structure of the patient's missing spinous process and is therefore designed to be used as a replacement for the missing bone.

The main portion 2 can be provided in different sizes to fit the anatomy of the patient in the best possible way.

Advantageously, the main portion 2 presents a plurality of lightening holes 6 which reduce the weight of the main portion creating a lightweight device.

In order to firmly arrange the main portion 2 in the correct position at the missing spinous process, a spinal fixing equipment 10 is needed.

In particular, the spinal fixing equipment 10 also comprises, in addition to the reconstruction device 1 described above, a pair of longitudinal bars 11 to which the reconstruction device 1 is fixed.

The longitudinal side bars 11 are able to be arranged in a sagittal direction Y alongside the real spinous processes 9 of the cervical and/or spinal vertebrae and are fixed to the vertebrae by means of polyaxial screws of known type.

The connection between each of these longitudinal bars 11 and the transverse fixing bar 4 of the reconstruction device 1 takes place via a respective transverse connection element 12.

The connection element 12 comprises a main body 13 which presents at least a first 13a and a second 13b housing seat, respectively for one of the two longitudinal bars 11 and for the transverse fixing bar 4.

Advantageously, the first 13a and second 13b housing seats provided in the main body 13 are arranged on parallel planes and extend along transversely reciprocal axial directions, following the spatial arrangement of the bars 11 and 4.

Preferably, the first seat 13a is partially open and is defined by a groove formed on a side surface of the main body 13.

In this way, the insertion of the bar within it can also be achieved laterally.

The second seat 13b, instead, is defined by a through-hole inside the main body 13.

The development axis 13a' of the first seat 13a is preferably orthogonal to the axis of development 13b' of the second seat 13b. The two seats 13a and 13b, preferably presenting a substantially cylindrical shape, are communicating with each other.

The connecting element 12 also comprises tightening means 14 for blocking any roto-translational movement of the longitudinal bar 11 and of the transverse bar 4: in particular, the tightening means 14 securing the bars 11 and 4 in an operative position with respect to the main body 13 and prevent relative movements between the two bars.

Preferably, the tightening means 14 comprise a fastening screw.

Advantageously, the tightening means 14 are arranged inside a respective housing 15 formed inside the main body 13.

Preferably, the housing 15 is a cylindrical cavity whose axis 15a extends along a direction orthogonal to the direction of development axes 13a' and 13b' of the first 13a and second 13b seats.

Moreover, the housing 15 is in communication with the second seat 13b and, consequently, with the first seat 13a.

By acting on the tightening means 14, bars 11 and 4 are blocked in their respective seats 13a and 13b.

Before fixing the bars in their final position, it is necessary to make precise and accurate adjustments.

In this regard, it is preferable that at least one of the two bars is prevented from sliding freely inside its seat.

For this purpose, inside the connection element 12, in particular inside the main body 13, there are specific interference means 16 adapted to restrain the sliding of at least the transverse fixing bar 4 within the respective housing seat 13b.

Advantageously, said interference means 16 are arranged inside a respective housing 17 which is in communication with the second seat 13b.

The interference means 16 face the interior of the second housing seat 13b, reducing the passage opening of the bar and interfering with it by friction.

The embodiment illustrated in the attached drawings shows the housing 17 of the interference means 16 developing along a direction orthogonal to the direction of development axes 13a' and 13b' of the first 13a and second 13b seats. Other positions and orientations of the housing 17 are validly possible, provided there is an interference with one of the two bars.

The interference means 16 can be done in different ways and advantageously comprise an elastic element adapted to exert a pressure force against the transverse fixing bar 4.

Still more preferably, the elastic element is a wire spring.

A first assembly method requires that, after having positioned and fixed the two longitudinal bars 11 to the vertebrae, a connection element 12 is applied on each longitudinal bar 11, by inserting the latter inside the first seat 13a.

Subsequently the transverse fixing bar 4 is inserted within the second seat 13b.

Alternatively, a second assembly procedure requires positioning and fixing the two longitudinal bars 11 to the vertebrae, separately assembling the system comprising the two connection elements 12 and the reconstruction device 1 interposed between them, and then placing this system first on a bar longitudinal 11 and, subsequently, on the other.

Before completely blocking the system with the tightening means 14, the connection element is adjusted by correcting the position along the respective longitudinal bar 11 and by setting the position of the transverse fixing bar 4 so as to improve its fitting to the spinal fixing system. It is also possible to rotate the connection element 12 by a few degrees around the longitudinal bar 11, compatibly with the elasticity and the interference produced by the transverse fixing bar 4.

The transverse fixing bar 4, inserted inside the second seat 13b, reaches the interference means 16 having a retentive effect on it, preventing it from slipping off the respective seat 13a before the action of the tightening means 14 intervenes.

By acting on the tightening means 14, the screw is pushed further down within its housing 15, until it protrudes into the second seat 13b in which the transverse fixing bar 4 is inserted.

The transverse fixing bar 4 insists and rests partially on both longitudinal bars 11 housed inside the respective groove or first seat 13a.

The action of pressure exerted by the fixing screw 14 on the transverse fixing bar 4 is discharged on each longitudinal bar 11 that is counteracted by the bottom of the first seat 13a.

In this way, each longitudinal bar 11 is fixed to the transverse fixing bar 4 within the respective seats 13a and 13b, preventing relative movement both between the bars and of each bar with respect to the connection element 12 itself.

The invention achieves the intended objects and achieves important advantages.

The device for reconstructing a spinous process allows to recreate the missing natural spinous process due to breakage or bone resections, fills the space between the missing vertebrae, and restores bone appearance.

Moreover, it provides anchoring points for ligaments, giving the opportunity to attach ligaments, thus restoring their natural functionality and the original anatomical pattern. The transverse connection achieved by the transverse fixing bar improves the torsional functionality of the system.

The main purpose of this device for reconstructing a spinous process is to act as a bridge between adjacent vertebrae, when the natural spinous process is absent.

The spinal fixing equipment allows to place and secure in the correct position the device for reconstructing the spinous process.

The invention claimed is:

1. A device for reconstructing a spinous process of a vertebrae, comprising:

a main portion having a first surface and a second surface, the first surface and the second surface being opposite and spaced apart from each other, the main portion defining at least one engaging hole and at least one through-seat, wherein the engaging hole and the through-seat extend through the first and second surfaces, and the at least one through-seat is configured for the insertion of ligaments to be reconstructed;

one fixing bar transversely insertable into the engaging hole, wherein said device is fixable to the vertebrae, so that said main portion is configured for replacing the spinous process of the vertebrae to be reconstructed, wherein said fixing bar is realized in a single body, and wherein said first and second surfaces of the main portion are tapered and each surface comprises a widened portion and a narrow portion positioned at the opposite end of the main portion with respect to the widened portion, wherein the widened portion defines the engaging hole for the fixing bar.

2. The device according to claim 1, wherein the engaging hole comprises a polygonal geometry compatible and coupleable with a coupling portion of said fixing bar.

3. The device according to claim 1, wherein said main portion defines a plurality of lightening holes.

4. The device according to claim 3, wherein the device comprises a fastening pin able to block said main portion in a position along an axis of said transverse fixing bar.

5. A spinal fixing equipment, comprising:
a main portion having a first surface and a second surface, the first surface and the second surface being opposite and spaced apart from each other, the main portion defining at least one engaging hole and at least one through-seat for inserting ligaments to be reconstructed, wherein the engaging hole and the through-seat extend through the first and second surfaces;

one transverse fixing bar transversely insertable into the engaging hole;

a pair of side longitudinal bars suitable for being arranged in a sagittal direction along the sides of the spinous processes of the cervical and/or spinal vertebrae; and a connection element between each of said longitudinal bars and said transverse fixing bar.

6. The fixing equipment according claim 5, wherein the connection element comprises:
a main body comprising at least a first housing seat for one of the two longitudinal bars, and a second housing seat for the transverse fixing bar;

tightening means which locks the pair of longitudinal bars and the fixing bar in an operative position with respect to the main body and preventing relative movements between said bars; and interference means which restrains the sliding at least of the transverse fixing bar within the respective seat.

7. The fixing equipment according to claim 6, wherein the first and second housing seats are arranged on parallel planes and extend along directions transverse to each other.

8. The fixing equipment according to claim 7, wherein the first seat is defined by a partially open groove formed in the main body.

9. The fixing equipment according to claim 7, wherein the second seat defines a through hole inside the main portion.

10. The fixing equipment according to claim 6, wherein said first seat is in communication with said second seat.

11. The fixing equipment according to claim 6, wherein the interference means projects within the first or second seat.

12. The fixing equipment according to claim 11, wherein the interference means comprises an elastic member suitable for applying a pressure force against the transverse fixing bar.

13. The fixing equipment according to claim 12, wherein the elastic member is a spring wire protruding within the second housing seat.

14. The fixing equipment according to claim 6, wherein the tightening means includes a fastening screw.

15. The fixing equipment according to claim 6, wherein the interference means and the tightening means act inside a respective housing each extending along a direction orthogonal to the axial extension direction of the first and second seats.

16. The fixing equipment according to claim 15, wherein the housing for the interference means and the housing for the tightening means are in communication with the second seat.

* * * * *